United States Patent
Clark et al.

(10) Patent No.: US 8,222,468 B2
(45) Date of Patent: Jul. 17, 2012

(54) ORGANIC COMPOUND CONVERSION PROCESS

(75) Inventors: Michael C. Clark, Chantilly, VA (US); Teng Xu, Hampton, NJ (US); Matthew J. Vincent, Baytown, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 535 days.

(21) Appl. No.: 12/299,276

(22) PCT Filed: May 8, 2006

(86) PCT No.: PCT/US2006/017734
§ 371 (c)(1), (2), (4) Date: Jun. 8, 2009

(87) PCT Pub. No.: WO2007/130055
PCT Pub. Date: Nov. 15, 2007

(65) Prior Publication Data
US 2009/0281361 A1    Nov. 12, 2009

(51) Int. Cl.
C07C 2/66 (2006.01)
C07C 6/12 (2006.01)
(52) U.S. Cl. .......... 585/467; 585/475; 585/323
(58) Field of Classification Search .......... 585/467, 585/475, 323
See application file for complete search history.

(56) References Cited

U.S. PATENT DOCUMENTS

| | | |
|---|---|---|
| 3,308,069 A | 3/1967 | Wadlinger et al. |
| 3,449,070 A | 6/1969 | McDaniel et al. |
| 3,751,504 A | 8/1973 | Keown et al. |
| 3,766,093 A | 10/1973 | Chu |
| 3,894,104 A | 7/1975 | Chang et al. |
| 4,016,218 A | 4/1977 | Haag et al. |
| 4,415,438 A | 11/1983 | Dean et al. |
| 4,439,409 A | 3/1984 | Puppe et al. |
| 4,547,605 A | 10/1985 | Kresge et al. |
| 4,826,667 A | 5/1989 | Zones et al. |
| 4,891,458 A | 1/1990 | Innes et al. |
| 4,916,097 A | 4/1990 | Chu et al. |
| 4,954,325 A | 9/1990 | Rubin et al. |
| 4,956,514 A | 9/1990 | Chu |

(Continued)

FOREIGN PATENT DOCUMENTS

EP    0134331    3/1985

(Continued)

OTHER PUBLICATIONS

Xu, T. et al., "*The Development and applications of CAVERN methods for in situ NMR studies of reactions on solid acids*", Topics in Catalysis, 1997, vol. 4, pp. 109-118.

(Continued)

*Primary Examiner* — Thuan Dinh Dang
(74) *Attorney, Agent, or Firm* — Darryl M. Tyus (57) ABSTRACT

The present invention provides a process for conversion of feedstock comprising organic compounds to desirable conversion product at organic compound conversion conditions in the presence of catalyst comprising an acidic, porous crystalline material and having a Proton Density Index of greater than 1.0, for example, from greater than 1.0 to about 2.0, e.g. from about 1.01 to about 1.85. The acidic, porous crystalline material of the catalyst may comprise a porous, crystalline material or molecular sieve having the structure of zeolite Beta, an MWW structure type material, e.g. MCM-22, MCM-36, MCM-49, MCM-56, or a mixture thereof.

13 Claims, 1 Drawing Sheet

U.S. PATENT DOCUMENTS

| | | |
|---|---|---|
| 4,992,606 A | 2/1991 | Kushnerick et al. |
| 5,107,049 A | 4/1992 | Le et al. |
| 5,134,242 A | 7/1992 | Le et al. |
| 5,146,029 A | 9/1992 | Bundens et al. |
| 5,236,575 A | 8/1993 | Bennett et al. |
| 5,250,277 A | 10/1993 | Kresge et al. |
| 5,264,643 A | 11/1993 | DiGuiseppi et al. |
| 5,334,795 A * | 8/1994 | Chu et al. .................. 585/467 |
| 5,362,697 A | 11/1994 | Fung et al. |
| 5,557,024 A | 9/1996 | Cheng et al. |
| 6,077,498 A | 6/2000 | Diaz Cabanas et al. |
| 6,231,751 B1 | 5/2001 | Canos et al. |
| 6,984,764 B1 | 1/2006 | Roth et al. |
| 2003/0028059 A1 | 2/2003 | Hamper et al. |

FOREIGN PATENT DOCUMENTS

| | | |
|---|---|---|
| EP | 0 293 032 | 7/1993 |
| EP | 1 242 343 | 9/2002 |
| WO | WO 00/35836 | 6/2000 |
| WO | 00/66263 | 11/2000 |
| WO | WO 00/66236 | 11/2000 |
| WO | WO 01/56960 | 8/2001 |
| WO | WO 2005/118476 | 12/2005 |
| WO | WO 2006/094008 | 9/2006 |
| WO | WO 2006/094010 | 9/2006 |
| WO | WO 2006/107452 | 10/2006 |
| WO | WO 2007/130055 | 11/2007 |

OTHER PUBLICATIONS

Cory, D.G. et al., "*Suppression of Signals from the Probe in Bloch Decay Spectra*", Journal of Magnetic Resonance, 1988, vol. 80, pp. 128-132.

PCT/US2006/017734, filed May 8, 2006, Inventors: Michael C. Clark et al., entitled "Organic Compound Conversion Process".

\* cited by examiner

ORGANIC COMPOUND CONVERSION PROCESS

CROSS REFERENCE TO RELATED APPLICATIONS

This is U.S. national stage application under 35 U.S.C. 371 of International Application PCT/US2006/017734 having an international filing date of 8 May 2006. The above application is fully incorporated herein by reference.

BACKGROUND OF THE INVENTION

The present invention relates to a process for conversion of feedstock comprising organic compounds. One embodiment of the present invention includes a mechanism for producing alkylaromatics, for example ethylbenzene and cumene. Another embodiment of the present invention includes a process for producing oligomers, for example dimers, trimers and tetramers of olefins, e.g. ethylene, propylene, butylene or mixtures thereof.

The alkylaromatic compounds ethylbenzene and cumene, for example, are valuable commodity chemicals which are used industrially for the production of styrene monomer and coproduction of phenol and acetone respectively. In fact, a common route for the production of phenol comprises a process which involves alkylation of benzene with propylene to produce cumene, followed by oxidation of the cumene to the corresponding hydroperoxide, and then cleavage of the hydroperoxide to produce equimolar amounts of phenol and acetone. Ethylbenzene may be produced by a number of different chemical processes. One process which has achieved a significant degree of commercial success is the vapor phase alkylation of benzene with ethylene in the presence of a solid, acidic ZSM-5 zeolite catalyst. Examples of such ethylbenzene production processes are described in U.S. Pat. Nos. 3,751,504 (Keown), 4,547,605 (Kresge) and 4,016,218 (Haag).

Another process which has achieved significant commercial success is the liquid phase process for producing ethylbenzene from benzene and ethylene since it operates at a lower temperature than the vapor phase counterpart and hence tends to result in lower yields of by-products. For example, U.S. Pat. No. 4,891,458 (Innes) describes the liquid phase synthesis of ethylbenzene with zeolite Beta, whereas U.S. Pat. No. 5,334,795 (Chu) describes the use of MCM-22 in the liquid phase synthesis of ethylbenzene.

Cumene has for many years been produced commercially by the liquid phase alkylation of benzene with propylene over a Friedel-Craft catalyst, particularly solid phosphoric acid or aluminum chloride. More recently, however, zeolite-based catalyst systems have been found to be more active and selective for propylation of benzene to cumene. For example, U.S. Pat. No. 4,992,606 (Kushnerick) describes the use of MCM-22 in the liquid phase alkylation of benzene with propylene.

Existing alkylation processes for producing alkylaromatic compounds, for example ethylbenzene and cumene, inherently produce polyalkylated species as well as the desired monoalkyated product. It is therefore normal to transalkylate the polyalkylated species with additional aromatic feed, for example benzene, to produce additional monoalkylated product, for example ethylbenzene or cumene, either by recycling the polyalkylated species to the alkylation reactor or, more frequently, by feeding the polyalkylated species to a separate transalkylation reactor. Examples of catalysts which have been used in the alkylation of aromatic species, such as alkylation of benzene with ethylene or propylene, and in the transalkylation of polyalkylated species, such as polyethylbenzenes and polyisopropylbenzenes, are listed in U.S. Pat. No. 5,557,024 (Cheng) and include MCM-22, PSH-3, SSZ-25, zeolite X, zeolite Y, zeolite Beta, acid dealuminized mordenite and TEA-mordenite. Transalkylation over a small crystal (<0.5 micron) form of TEA-mordenite is also disclosed in U.S. Pat. No. 6,984,764.

Where the alkylation step is performed in the liquid phase, it is also desirable to conduct the transalkylation step under liquid phase conditions. However, by operating at relatively low temperatures, liquid phase processes impose increased requirements on the catalyst, particularly in the transalkylation step where the bulky polyalkylated species must be converted to additional monoalkylated product without producing unwanted by-products. This has proven to be a significant problem in the case of cumene production where existing catalysts have either lacked the desired activity or have resulted in the production of significant quantities of by-products such as ethylbenzene and n-propylbenzene.

According to the present invention, it has now unexpectedly been found that an organic compound conversion process conducted in the presence of a specific catalyst manufactured to exhibit a Proton Density Index ("PDI"), as herein defined, of greater than 1.0, for example, from greater than 1.0 to about 2.0, e.g. from about 1.01 to about 1.85, yields a unique combination of activity and, often importantly, selectivity. This is especially the case when the process involves liquid phase alkylation for manufacture of monoalkylated product, particularly for the liquid phase alkylation of benzene to ethylbenzene, cumene or sec-butylbenzene. This obviates or reduces the demand in many instances for the difficult transalkylation reaction for conversion of unwanted bulky polyalkylated species in such a process.

SUMMARY OF THE INVENTION

According to the present invention, there is provided a process for conversion of a feedstock comprising organic compounds to desirable conversion product at organic compound conversion conditions in the presence of catalyst comprising an acidic, porous crystalline material and having a PDI of greater than 1.0, for example, from greater than 1.0 to about 2.0, e.g. from about 1.01 to about 1.85. According to one aspect of the invention, there is provided a process for selectively producing a desired monoalkylated aromatic compound comprising the step of contacting an alkylatable aromatic compound with an alkylating agent in the presence of catalyst under at least partial liquid phase conditions, said catalyst comprising an acidic, porous crystalline material and having a PDI of greater than 1.0, for example, from greater than 1.0 to about 2.0, e.g. from about 1.01 to about 1.85. Another aspect of the present invention is an improved alkylation process for the selective production of monoalkyl benzene comprising the step of reacting benzene with an alkylating agent under alkylation conditions in the presence of alkylation catalyst which comprises an acidic, porous crystalline material and having a PDI of greater than 1.0, for example, from greater than 1.0 to about 2.0, e.g. from about 1.01 to about 1.85. Still another aspect of the present invention is an improved oligomerization process comprising contacting feedstock comprising olefins, for example ethylene, propylene and/or the butenes, with catalyst at oligomerization reaction conditions to produce desirable distributions of oligomers, said catalyst comprising an acidic, porous crystalline material and having a PDI of greater than 1.0, for example, from greater than 1.0 to about 2.0, e.g. from about 1.01 to about 1.85. The catalyst for use in the present process may comprise, for example, an acidic, porous crystalline material or molecular sieve having the structure of zeolite Beta, or one having an X-ray diffraction pattern including d-spacing maxima at 12.4±0.25, 6.9±0.15, 3.57±0.07 and 3.42±0.07 Angstroms, said catalyst having a PDI of greater than 1.0, for example, from greater than 1.0 to about 2.0, e.g. from about 1.01 to about 1.85. More particularly, the catalyst for use herein may comprise an acidic, porous crystalline material or molecular sieve having the structure of zeolite Beta, an MWW structure type material, e.g. MCM-22, or a mixture thereof.

The catalyst for use in the present invention preferably comprises an MWW structure type material, such as for example an acidic, porous crystalline silicate having the structure of MCM-22, PSH-3, SSZ-25, ERB-1, ITQ-1, ITQ-2, ITQ-30, MCM-36, MCM-49, MCM-56 and mixtures thereof.

DETAILED DESCRIPTION OF THE INVENTION

The present invention relates to a process for conversion of feedstock comprising organic compounds. One such process mechanism involves production of monoalkylated aromatic compounds, particularly ethylbenzene, cumene and sec-butylbenzene, by the liquid or partial liquid phase alkylation of an alkylatable aromatic compound, particularly benzene. An example of another process mechanism of the present invention involves production of olefin oligomers, particularly lower molecular weight oligomers. More particularly, the present process uses a catalyst composition comprising an acidic, porous crystalline material and is manufactured to exhibit a PDI of greater than 1.0, for example, from greater than 1.0 to about 2.0, e.g. from about 1.01 to about 1.85.

As used herein, the term PDI when used in connection with a particular catalyst composition is defined as the proton density of the new, treated, catalyst composition measured at a given temperature, divided by the proton density of the original, untreated, catalyst composition measured at the same given temperature.

As used herein, the term "proton density" means the millimoles (mmol) of acidic protons and/or non-acidic protons per gram of catalyst composition. The proton density of the new, treated catalyst composition, and the proton density of the original, untreated catalyst composition are both measured at the same temperature, for example room temperature, e.g. from about 20° C. to about 25° C.

The amount of protons on a catalyst sample is measured by a solid-state nuclear magnetic resonance method for characterizing the amount of acidic protons and non-acidic protons on such catalyst sample as disclosed herein. These acidic and non-acidic protons may be present as any hydrogen-containing moiety, or proton-containing moiety, including, but not limited to H, $H^+$, OH, $OH^-$, and other species. The nuclear magnetic resonance method includes, but is not limited to, magic angle spinning (MAS) NMR. Sample preparation is the key in NMR measurement of the amount of such protons on the catalyst samples. A trace amount of water will strongly distort the $^1H$ NMR intensity due in part to the fast $^1H$ chemical exchange involving Bronsted acid sites and a water molecule.

The method for producing the catalyst for use in the present invention comprises the steps of:

(a) providing a first, untreated catalyst, i.e. one not having been treated according to steps (b) and (c) of this method, comprising an acidic, porous crystalline material, said first, untreated catalyst having a first hydration state measured in mmol of protons per gram of catalyst;

(b) contacting the first, untreated catalyst of step (a) with water in liquid or gaseous form, at a contact temperature of up to about 500° C., such as from about 1° C. to about 500° C., preferably from about 1° C. to about 99° C., for a contact time of at least about 1 second, preferably from about 1 minute to about 60 minutes, to generate a second catalyst having a second hydration state measured in mmol of protons per gram of catalyst, said second hydration state being greater than said first hydration state, i.e. the product of step (b) has a higher proton density than the step (a) catalyst; and (c) drying the second catalyst resulting from step (b) at a drying temperature of up to about 550° C., preferably from about 20° C. to about 550° C., more preferably from about 100° C. to about 200° C., for a drying time of at least about 0.01 hour, preferably from about 0.1 to about 24 hours, more preferably from about 1 to about 6 hours, to generate the catalyst composition having a third hydration state measured in mmol of protons per gram of catalyst between said first and second hydration states. The step (c) product will have a Proton Density Index of greater than 1.0, for example, from greater than 1.0 to about 2.0, e.g. from about 1.01 to about 1.85.

During drying step (c), acidic protons and/or non-acidic protons are removed from the catalyst contacted with water in liquid or gaseous form in accordance with step (b). However, care must be taken during drying step (c) to avoid removal of essentially all acidic and/or non-acidic protons of the catalyst resulting from step (b). The hydration state of the step (c) product will be higher than that of the starting step (a) catalyst and lower than that of the step (b) product. It is recognized that increases in proton density are not simply the conversion of Lewis acid sites to Bronsted acid sites. Not wishing to be bound by any theory of operation, it is believed that contacting a catalyst comprising an acidic, porous crystalline material and having a first hydration state with water in liquid or gaseous form under certain contact time and temperature conditions creates a catalyst having a second hydration state higher than the first hydration state. This, followed by drying under certain controlled drying time and temperature conditions may change the nature, type, and/or the amount of acidic and/or non-acidic protons on such catalyst which are associated with the chemical reaction, to generate a catalyst composition having a third hydration state between that of the first and second hydration states, whereby the catalyst composition will have a Proton Density Index of greater than about 1.0. That is, such catalyst comprising an acidic, porous crystalline material and treated by the above method has a greater proton density, and/or a greater number of acidic and/or non-acidic protons as compared to the same catalyst which is not treated by such method. In other words, PDI is defined as the proton density of the third hydration state catalyst composition divided by the proton density of that catalyst in the first hydration state, both prepared and measured in the same manner.

The term "aromatic" in reference to the alkylatable aromatic compounds which may be useful as feedstock herein is to be understood in accordance with its art-recognized scope. This includes alkyl substituted and unsubstituted mono- and polynuclear compounds. Compounds of an aromatic character that possess a heteroatom may also be useful.

Substituted aromatic compounds that can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the alkylation reaction.

Suitable aromatic compounds include benzene, naphthalene, anthracene, naphthacene, perylene, coronene, and phenanthrene, with benzene being preferred.

Generally the alkyl groups that can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, n-propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene, 1,2,3,4-tetraethylbenzene, 1,2,3,5-tetramethylbenzene, 1,2,4-triethylbenzene, 1,2,3-trimethylbenzene, m-butyltoluene, p-butyltoluene, 3,5-diethyltoluene, o-ethyltoluene, p-ethyltoluene, m-propyltoluene, 4-ethyl-m-xylene, dimethylnaphthalenes, ethylnaphthalene, 2,3-dimethylanthracene, 9-ethylanthracene, 2-methylanthracene, o-methylanthracene, 9,10-dimethylphenanthrene, and 3-methyl-phenanthrene. Higher molecular weight alkylaromatic compounds can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing a mixture of benzene, toluene and/or xylene constitutes a particularly useful feed for the alkylation process of this invention.

The alkylating agents that may be useful in the process of this invention generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes (including 1-butene, 2-butene and mixtures thereof), and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are useful as alkylating agents in the alkylation process of this invention. Also, such mixtures of light olefins are useful as reactants in the oligomerization processes of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents and oligomerization reactants herein. For example, a typical FCC light olefin stream possesses the following composition:

|           | Wt. % | Mole % |
|-----------|-------|--------|
| Ethane    | 3.3   | 5.1    |
| Ethylene  | 0.7   | 1.2    |
| Propane   | 4.5   | 15.3   |
| Propylene | 42.5  | 46.8   |
| Isobutane | 12.9  | 10.3   |
| n-Butane  | 3.3   | 2.6    |
| Butenes   | 22.1  | 18.32  |
| Pentanes  | 0.7   | 0.4    |

Reaction products that may be obtained from the process of the present invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes, a mixture of heavier olefins from the oligomerization of light olefins. Particularly preferred process mechanisms of the invention relate to the production of cumene by the alkylation of benzene with propylene, production of ethylbenzene by the alkylation of benzene with ethylene, production of sec-butylbenzene by the alkylation of benzene with butenes, and oligomerization of ethylene, propylene, butylene, or mixtures thereof.

The organic conversion processes contemplated by this invention include, but are not limited to, alkylation of aromatic compounds and oligomerization of olefins and may be conducted such that the reactants are brought into contact with the required catalyst in a suitable reaction zone such as, for example, in a flow reactor containing a fixed bed of the catalyst composition, under effective conversion conditions. Such conditions include a temperature of from about 0° C. to about 1000° C., preferably from about 0° C. to about 800° C., a pressure of from about 0.1 to about 1000 atmospheres, preferably from about 0.125 to about 500 atmospheres, and a feed weight hourly space velocity (WHSV) of from about 0.01 to 500 hr$^{-1}$, preferably from about 0.1 to about 100 hr$^{-1}$. If a batch reactor is used, the reaction time will be from about 1 minute to about 100 hours, preferably from about 1 hour to about 10 hours.

The reactants can be in either the vapor phase or partially or completely in the liquid phase and can be neat, i.e. free from intentional admixture or dilution with other material, or they can be brought into contact with the catalyst composition with the aid of carrier gases or diluents such as, for example, hydrogen or nitrogen.

An alkylation process of this invention may be conducted such that the organic reactants, i.e., the alkylatable aromatic compound and the alkylating agent, are brought into contact with a suitable alkylation catalyst in a suitable reaction zone such as, for example, in a flow reactor containing a fixed bed of such catalyst, under effective alkylation conditions. The alkylation catalyst may comprise one or a mixture of an acidic, porous crystalline materials or molecular sieves having the structure of zeolite Beta, zeolite Y, mordenite or an MWW structure type material having an X-ray diffraction pattern including d-spacing maxima at 12.4±0.25, 6.9±0.15, 3.57±0.07 and 3.42±0.07 Angstroms. Such suitable alkylation conditions include a temperature of from about 0° C. to about 500° C., preferably from about 10° C. to about 260° C., a pressure of from about 0.2 to about 250 atmospheres, preferably from about 1 to about 55 atmospheres, a molar ratio of alkylatable aromatic compound to alkylating agent of from about 0.1:1 to about 50:1, preferably from about 0.5:1 to about 10:1, and a feed weight hourly space velocity (WHSV) based on the alkylating agent of from about 0.1 to 500 hr$^{-1}$, preferably from about 0.5 to about 100 hr$^{-1}$.

When benzene is alkylated with ethylene to produce ethylbenzene, the alkylation reaction is preferably carried out in the liquid phase under conditions including a temperature of from about 150° C. to about 300° C., more preferably from about 170° C. to about 260° C.; a pressure up to about 200 atmospheres, more preferably from about 20 atmospheres to about 55 atmospheres; a weight hourly space velocity (WHSV) based on the ethylene alkylating agent of from about 0.1 to about 20 hr$^{-1}$, more preferably from about 0.5 to about 6 hr$^{-1}$; and a ratio of benzene to ethylene in the alkylation reactor of from about 0.5:1 to about 30:1 molar, more preferably from about 1:1 to about 10:1 molar.

When benzene is alkylated with propylene to produce cumene, the reaction may also take place under liquid phase conditions including a temperature of up to about 250° C., preferably up to about 150° C., e.g., from about 10° C. to about 125° C.; a pressure of about 250 atmospheres or less, e.g., from about 1 to about 30 atmospheres; a weight hourly space velocity (WHSV) based on propylene alkylating agent of from about 0.1 hr$^{-1}$ to about 250 hr$^{-1}$, preferably from about 1 hr$^{-1}$ to about 50 hr$^{-1}$; and a ratio of benzene to propylene in the alkylation reactor of from about 0.5:1 to about 30:1 molar, more preferably from about 1:1 to about 10:1 molar.

When benzene is alkylated with an alkylating agent selected from the group consisting of 1-butene, 2-butene and mixtures thereof, to produce sec-butylbenzene, the reaction may also take place under liquid phase conditions including a temperature of from about 50 to about 250° C., preferably from about 100 to about 200° C.; a pressure of about 3.5 to about 35 atmospheres, preferably from about 7 to about 27 atmospheres; a WHSV based on the butene alkylating agent of from about 0.1 to about 20 hr$^{-1}$, preferably from about 1 to about 10 hr$^{-1}$; and a ratio of benzene to the butene alkylating agent from about 1:1 to about 10:1, preferably from about 1:1 to about 4:1 molar.

The catalyst for use in the present invention may comprise one or more acidic, porous crystalline materials or molecular sieves having the following structure: zeolite Beta (described in U.S. Pat. No. 3,308,069); or an MWW structure type such as, for example, those having an X-ray diffraction pattern including d-spacing maxima at 12.4±0.25, 6.9±0.15, 3.57±0.07 and 3.42±0.07 Angstroms.

As used herein, an "acidic, porous crystalline material" means a porous crystalline material or molecular sieve containing acidic protons sufficient to catalyze hydrocarbon conversion reactions.

Examples of MWW structure type materials include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in U.S. Pat. No. 6,231,751), ITQ-30 (described in WO 2005-118476), MCM-36 (described in U.S. Pat. No. 5,250,277), MCM-49 (described in U.S. Pat. No. 5,236,575) and MCM-56 (described in U.S. Pat. No. 5,362,697). The catalyst can include the acidic, porous crystalline material or molecular sieve in unbound or self-bound form or, alternatively, the material or molecular sieve can be combined in a conventional manner with an oxide binder as hereinafter detailed. For certain applications of the catalyst, the average particle size of the acidic, porous crystalline material or molecular sieve component may be from about 0.05 to about 200 microns, for example, from 20 to about 200 micron.

When the reaction mechanism of the present invention is alkylation, the alkylation reactor effluent contains excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the distillation may be further distilled to separate monoalkylated product from polyalkylated products and other heavies.

The polyalkylated products separated from the alkylation reactor effluent may be reacted with additional aromatic feed in a transalkylation reactor, separate from the alkylation reactor, over a suitable transalkylation catalyst. The transalkylation catalyst may comprise one or a mixture of acidic, porous crystalline materials having the structure of zeolite Beta, zeolite Y, mordenite or an MWW structure type material having an X-ray diffraction pattern including d-spacing maxima at 12.4±0.25, 6.9±0.15, 3.57±0.07 and 3.42±0.07 Angstroms.

The X-ray diffraction data used to characterize said above catalyst structures are obtained by standard techniques using the K-alpha doublet of copper as the incident radiation and a diffractometer equipped with a scintillation counter and associated computer as the collection system. Materials having the above X-ray diffraction lines include, for example, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in U.S. Pat. No. 6,231,751), ITQ-30 (described in WO 2005-118476), MCM-36 (described in U.S. Pat. No. 5,250,277), MCM-49 (described in U.S. Pat. No. 5,236,575) and MCM-56 (described in U.S. Pat. No. 5,362,697), with MCM-22 being particularly preferred.

Zeolite Beta is disclosed in U.S. Pat. No. 3,308,069. Zeolite Y and mordenite occur naturally but may also be used in one of their synthetic forms, such as Ultrastable Y (USY), which is disclosed in U.S. Pat. No. 3,449,070, Rare earth exchanged Y (REY), which is disclosed in U.S. Pat. No. 4,415,438, and TEA-mordenite (i.e., synthetic mordenite prepared from a reaction mixture comprising a tetraethylammonium directing agent), which is disclosed in U.S. Pat. Nos. 3,766,093 and 3,894,104. However, in the case of TEA-mordenite for use in the transalkylation catalyst, the particular synthesis regimes described in the patents noted lead to the production of a mordenite product composed of predominantly large crystals with a size greater than 1 micron and typically around 5 to 10 micron. It has been found that controlling the synthesis so that the resultant TEA-mordenite has an average crystal size of less than 0.5 micron results in a transalkylation catalyst with materially enhanced activity for liquid phase aromatics transalkylation.

The small crystal TEA-mordenite desired for transalkylation can be produced by crystallization from a synthesis mixture having a molar composition within the following ranges:

|  | Useful | Preferred |
| --- | --- | --- |
| R/R + Na$^+$ = | >0.4 | 0.45-0.7 |
| OH$^-$/SiO$_2$ = | <0.22 | 0.05-0.2 |
| Si/Al$_2$ = | >30-90 | 35-50 |
| H$_2$O/OH = | 50-70 | 50-60 |

The crystallization is conducted at a temperature of 90 to 200° C., for a time of 6 to 180 hours.

The catalyst for use in the present invention may include an inorganic oxide material matrix or binder. Such matrix materials include synthetic or naturally occurring substances as well as inorganic materials such as clay, alumina, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

Specific useful catalyst matrix or binder materials employed herein include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of the acidic, porous crystalline materials or molecular sieve and binder or matrix, if present, may vary widely with the crystalline material or molecular sieve content ranging from about 1 to about 99 percent by weight, and more usually in the range of about 30 to about 80 percent by weight of the total catalyst. Of course, the catalyst may comprise a self-bound material or molecular sieve or an unbound material or molecular sieve, thereby being about 100% acidic, porous crystalline material or molecular sieve.

The catalyst for use in the present invention, or its acidic, porous crystalline material or molecular sieve component, may or may not contain added functionalization, such as, for example, a metal of Group VI (e.g. Cr and Mo), Group VII (e.g. Mn and Re) or Group VIII (e.g. Co, Ni, Pd and Pt), or phosphorus.

Experimental Methods

The following equipment and feed pretreatment methods were used in the experiments described in the non-limiting examples of the invention.

Equipment

A 300 ml Parr batch reaction vessel equipped with a stir rod and static catalyst basket was used for the activity and selectivity measurements. The reaction vessel was fitted with two removable vessels for the introduction of benzene and propylene respectively.

Feed Pretreatment

Commercial grade benzene was pretreated with molecular sieve 13×, molecular sieve 4A, Engelhard F-24 Clay, and Selexsorb CD. Polymer grade propylene obtained from a commercial specialty gases source was pretreated with molecular sieve 5A and Selexsorb CD. Ultra high purity grade nitrogen obtained from a commercial specialty gases source was pretreated with molecular sieve 5A and Selexsorb CD. All feed pretreatment materials were dried in a 260° C. oven for 12 hours before using. All references to benzene, propylene and nitrogen, refer to the commercial grade benzene, the polymer grade propylene, and the ultra high purity grade nitrogen, that have been pretreated as described herein.

The following NMR procedure for determining proton density was used in the experiments described in the non-limiting examples of the invention.

NMR Procedure for Determining Proton Density

Figure 1:
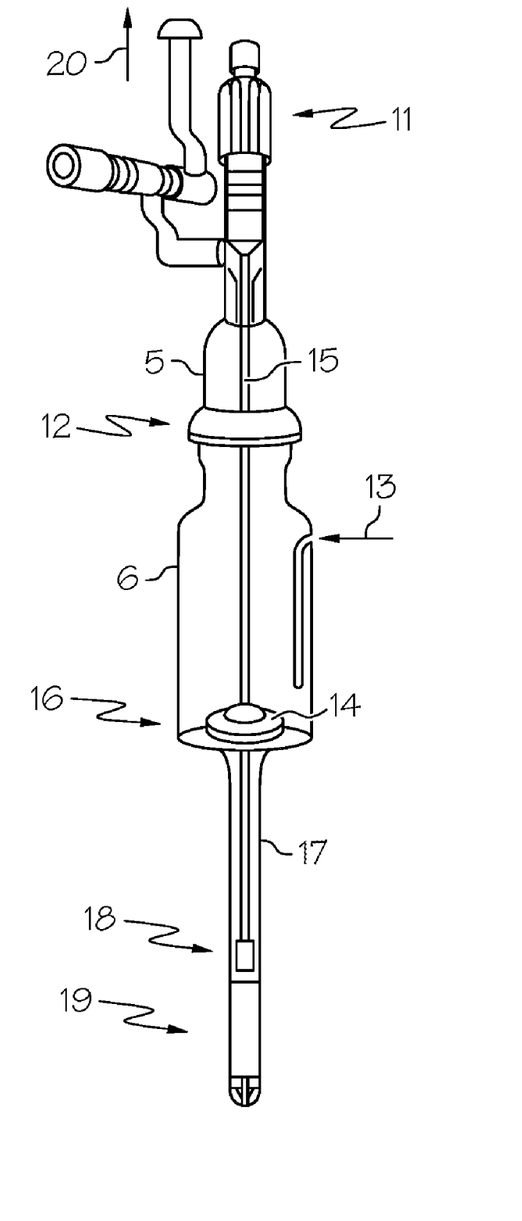
FIG. 1 shows the shallow bed CAVERN device used in experiments involving the present invention.

In the present invention, the NMR procedure for determining the proton density of a catalyst sample is as follows. The proton density of a catalyst sample may be determined using a shallow bed CAVERN device, shown in FIG. 1. In FIG. 1, a CAVERN device is shown which is comprised of an upper housing 5 and lower housing 6 connected by joint 12, having a mechanism 11 for lifting a glass trapdoor 16 over a catalyst bed 14, means for a vacuum line 20, and means for heating via thermocouple 13. A 5 mm o.d. glass tube 17 slides over a 3 mm stainless steel rod 15, and rests between the endcap 18 and the glass trapdoor 16. The stainless steel rod 15 is retracted by turning the mechanism II, whereby the glass tube 17 raises the glass trapdoor 16 above the catalyst bed 14. By gently turning or shaking the CAVERN device, the catalyst sample (not shown) falls into the MAS rotor 19. This process works for zeolites and metal oxide powders. Further details regarding the operation of the CAVERN device are disclosed in Xu, T.; Haw, J. F. *Top. Catal.* 1997, 4, 109-118, incorporated herein by reference.

In order to determine the proton density of a catalyst sample, a thin layer of the catalyst sample was spread out in the catalyst bed 14 of the CAVERN device, and the temperature of the catalyst sample via thermocouple 13 was raised to the desired temperature for evaluating the catalyst sample ("Specified NMR Pretreatment Temperature") under sufficient vacuum by vacuum line 20 to remove any moisture absorbed on the catalyst sample. The catalyst sample was typically held at the desired temperature for 2 hours under such vacuum prior to NMR measurement.

The thus prepared catalyst sample was loaded into a 5 mm NMR rotor, such as MAS rotor 19, and the rotor was sealed with a Kel-F end cap by manipulating the CAVERN device. All the operations were performed while the catalyst sample was still under vacuum, ensuring the sample integrity for NMR study. After the desired NMR spectra were acquired, the weight of MAS rotor 19, the catalyst sample and the endcap 18 was determined followed by weight determination of the rotor and the endcap 18 upon unpacking the catalyst sample. The difference in the two weights was the amount of the catalyst sample in the MAS rotor 19.

$^1$H NMR experiments were performed on a 400 MHz solid state NMR spectrometer operating at 399.8 MHz for $^1$H. Quantitative $^1$H spectra were obtained by the use of rotor-synchronized spin-echo sequence ($\pi/2$-$t_{D1}$-$\pi$-$t_{D2}$-Echo) using 8 to 12 kHz spinning speeds. Typically, 3.5-μs $\pi/2$ pulses, $t_{D1}$ of 125-μs and $t_{D2}$ of 113.1 μs were used for a spinning speed of 9 kHz. Spectra acquired using the solid echo sequence showed some background signal, presumably from the spinning module and the endcap 18 of the MAS rotor 19. A solid echo sequence with DEPTH removes the background signal from the spectra. The DEPTH sequence consisted of a 90° pulse (3.5-μs) followed by two 180° pulses. A description of the DEPTH sequence appears in Corey, D. G.; Ritchey, W. M. *J. Magn. Reson.* 1988, 80, 128, incorporated herein by reference. A pulse delay of 10 seconds was sufficient for quantifying proton density of the catalyst samples tested. Acetone was used as secondary standard for $^1$H shift (2.1 ppm). All the reported chemical shifts were referenced to tetramethylsilane (TMS) at 0 ppm.

The proton densities for various "as synthesized" acidic, porous crystalline materials not yet treated in accordance with the above method, and therefore in the first hydration state, are as follows:

| Acidic Porous Crystalline Material | Proton Density |
|---|---|
| Zeolite Beta | 3.10 mmol protons/gram zeolite Beta |
| MCM-22 | 2.24 mmol protons/gram MCM-22 |
| MCM-36 | 2.14-2.24 mmol protons/gram MCM-36 |
| MCM-49 | 2.14 mmol protons/gram MCM-49 |
| MCM-56 | 2.14-2.24 mmol protons/gram MCM-56 |

Of course, these acidic, porous crystalline materials in the third hydration state of having undergone treatment according to the above method would have proton densities greater than those listed above for the same material in the first hydration state.

The following method for determination of the Proton Density Index was used in the experiments described in the non-limiting examples of this invention.

Determination of Proton Density Index

The PDI of a particular catalyst composition is determined from the ratio of the proton density of the new, treated catalyst composition to the proton density of the original, untreated catalyst composition. Such new, treated catalyst composition may be treated in accordance with the proton adjustment techniques described herein or other techniques that alter proton density. Also, such original, untreated catalyst composition may or may not be treated in accordance with the proton adjustment techniques described herein or other techniques that alter proton density. As noted above, the term "proton density" as used herein means the millimoles (mmol) of acidic protons and/or non-acidic protons per gram of catalyst composition. The proton density of the new, treated catalyst composition, and the proton density of the original, untreated catalyst composition are both measured at the same temperature, for example room temperature, e.g. from about 20° C. to about 25° C. Therefore, the PDI of a particular catalyst composition is defined as the proton density of the new, treated, catalyst composition measured at a given temperature, divided by the proton density of the original, untreated, catalyst composition measured at the same given temperature.

The NMR spectrometer used to determine proton density was a Varian Infinity Plus 400 MHz solid state NMR with an Oxford AS400 magnet.

The following catalyst reactivity testing procedure was used in the non-limiting examples of the invention.

Catalyst Reactivity Testing Procedure

To prepare a catalyst composition for reactivity testing, a specified amount of a catalyst sample was dried in the presence of air in an oven at a specified ex-situ drying temperature ("Specified Ex-situ Drying Temperature") for 2 hours. The catalyst sample was removed from the oven and weighed. Quartz chips were used to line the bottom of a basket followed by loading of the catalyst sample into the basket on top of the first layer of quartz. Quartz chips were then placed on top of the catalyst sample. The basket containing the catalyst sample and quartz chips were placed in an oven at the Specified Ex-situ Drying Temperature in the presence of air for about 16 hours.

The reactor and all lines were cleaned with a suitable solvent (such as toluene) before each experiment. The reactor and all lines were dried in air after cleaning to remove all traces of cleaning solvent. The basket containing the catalyst sample and quartz chips were removed from the oven, immediately placed in the reactor, and the reactor was immediately assembled. The reactor temperature was set to an in-situ drying temperature ("Specified In-situ Drying Temperature") and purged with 100 SCCM of nitrogen for 2 hours.

The reactor temperature was then reduced to 130° C., the nitrogen purge was discontinued and the reactor vent closed. A 156.1 gram quantity of benzene was loaded into a 300 cc transfer vessel, performed in a closed system. The benzene vessel was pressurized to 100 psig with a nitrogen source and the benzene was transferred into the reactor. The agitator speed was set to 500 rpm and the reactor was allowed to equilibrate for 1 hour.

A 75 cc Hoke transfer vessel was then filled with 28.1 grams of liquid propylene and connected to the reactor vessel, and then connected with 300 psig nitrogen source. After the one-hour benzene stir time had elapsed, the propylene was transferred from the Hoke vessel to the reactor. The 300 psig nitrogen source was maintained connected to the propylene vessel and open to the reactor during the duration of the test to maintain constant reaction pressure of 300 psig. Liquid product samples were taken at 30, 60, 120, 150, 180 and 240 minutes after addition of the propylene. These samples were then analyzed by Gas Chromatography with a Flame Ionization Detector and procedures known to those skilled in the art.

In these examples, the selectivity of the catalyst sample ("Catalyst Selectivity") to the desired isopropylbenzene (cumene) product was calculated as the ratio of isopropylbenzene to diisopropylbenzene (IPB/DIPB) after propylene conversion reached 100%. A higher IPB/DIPB ratio means a greater selectivity of the catalyst sample to isopropylbenzene (cumene). Also, in these examples the catalytic activity of the catalyst samples was determined by calculating the 2nd order kinetic rate constant using mathematical techniques well known to those skilled in the art ("Catalyst Activity").

The following proton content adjustment techniques were used in the experiments described in the non-limiting examples of the invention.

Proton Content Adjustment Techniques

Proton Content Adjustment Technique #1

In one embodiment of the invention, a sample of catalyst comprising an acidic, porous crystalline material and having a first hydration state measured in millimoles (mmol) of protons per gram of catalyst, was placed into a suitable container. Water in liquid form, specifically deionized water, was transferred into the container slowly so as to displace air from the catalyst sample by filling from the bottom up. Water was added until the catalyst sample was completely covered with water and the level of the water was approximately ¼" above the catalyst sample. The catalyst sample and water were allowed to remain undisturbed under these conditions for a specified contact time ("Contact Time") of at least about 1 second preferably from about 1 minute to about 60 minutes or greater, to generate a catalyst sample having a second hydration state (measured in mmol of protons per gram of catalyst sample), in which the said second hydration state being greater that said first hydration state. After the Contact Time, the water was decanted and the catalyst sample was allowed to dry in air at ambient conditions for at least 8 hours, to generate a catalyst sample having a third hydration state (measured in mmol of protons per gram of catalyst sample).

Proton Content Adjustment Technique #2

In another embodiment of the invention, a sample of catalyst is exposed to water in the vapor form (with or without a suitable carrier, such as nitrogen) at a specified contact temperature ("Contact Temperature") and at a specified contact pressure ("Contact Pressure").

In still another embodiment of the invention, the catalyst sample that has first been treated in accordance with Proton Content Adjustment Technique #1 is then treated in accordance with Proton Content Adjustment Technique #2.

In still yet another embodiment of the invention, the catalyst sample that has first been treated in accordance with Proton Content Adjustment Technique #2 is then treated in accordance with Proton Content Adjustment Technique #1.

Non-limiting examples of catalyst samples made in accordance with the above described method, and the use of such catalyst samples in alkylation experiments, are described with reference to the following experiments.

Example 1

The catalyst sample of this Example 1 comprised 80 wt % MCM-49 and 20 wt % alumina ($Al_2O_3$) and its proton density was determined in accordance with the NMR Procedure for Determining Proton Density, described above, at the Specified NMR Pretreatment Temperature of 250° C. The proton density was 1.71 mmol per gram of catalyst (first hydration state).

A 0.5 gram portion of the catalyst sample of this Example 1 was tested in accordance with the Catalyst Reactivity Testing Procedure at the Specified Ex-situ Drying Temperature of 250° C. and the Specified In-situ Drying Temperature of 170° C. The Catalyst Selectivity of this catalyst sample was 5.92, determined as the weight ratio of isopropylbenzene to diisopropylbenzene (IPB/DIPB). The Catalyst Activity of this catalyst sample was 363.

Example 2

Another portion of the catalyst sample of Example 1 was treated in accordance with Proton Content Adjustment Technique #1 at a Contact Time of approximately 1 hour, to produce the treated catalyst sample of this Example 2 having a third hydration state. The proton density of the third hydration state of the treated catalyst sample was 1.85 mmol per gram of catalyst (third hydration state), determined in accordance with the NMR Procedure for Determining Proton Density, described above, at the Specified NMR Pretreatment Temperature of 250° C.

A 0.5 gram portion of the treated catalyst sample of this Example 2 was tested in accordance with the Catalyst Reactivity Testing Procedure at the Specified Ex-situ Drying Temperature of 250° C. and the Specified In-situ Drying Temperature of 170° C. The Catalyst Selectivity of this catalyst sample was 6.94, determined as the weight ratio of IPB/DIPB. The Catalyst Activity of this catalyst sample was 383.

The PDI of the catalyst sample of this Example 2 was determined to be 1.08, and represents an 8% increase in the proton content (determined as mmol of protons per gram of catalyst) as compared to the catalyst sample of Example 1. The Catalyst Selectivity (IPB/DIPB) of the catalyst sample of this Example 2 displayed an increase of 17%, and the Catalyst Activity displayed an increase of 5.5%, as compared to the catalyst sample of Example 1.

Example 3

The catalyst sample of this Example 3 comprised 80 wt % zeolite Beta and 20 wt % alumina and its proton density was determined in accordance with the NMR Procedure for Determining Proton Density, described above, at the Specified NMR Pretreatment Temperature of 250° C. The proton density was 2.48 mmol per gram of catalyst (first hydration state).

A 1.0 gram portion of the catalyst sample of this Example 3 was tested in accordance with the Catalyst Reactivity Testing Procedure at the Specified Ex-situ Drying Temperature of 250° C. and the Specified In-situ Drying Temperature of 170° C. The Catalyst Selectivity of this catalyst sample was 5.62, determined as the weight ratio of IPB/DIPB. The Catalyst Activity of this catalyst sample was 23.

Example 4

Another portion of the catalyst sample of Example 3 was treated in accordance with Proton Content Adjustment Technique #1 at a Contact Time of approximately 1 hour, to produce a treated catalyst of this Example 4 having a third hydration state. The proton density of the treated catalyst was 2.77 mmol per gram of catalyst (third hydration state), determined in accordance with the NMR Procedure for Determining Proton Density, described above, at the Specified NMR Pretreatment Temperature of 250° C.

A 1.0 gram portion of the treated catalyst of this Example 4 was tested in accordance with the Catalyst Reactivity Testing Procedure at the Specified Ex-situ Drying Temperature of 250° C. and the Specified In-situ Drying Temperature of 170° C. The Catalyst Selectivity of this catalyst sample was 9.35, determined as the weight ratio of IPB/DIPB. The Catalyst Activity of this catalyst sample was 4.

The PDI of the catalyst sample of this Example 4 was determined to be 1.12, and represents a 12% increase in proton content (determined as mmol of protons per gram of catalyst) as compared to the catalyst sample of Example 3. The Catalyst Selectivity (IPB/DIPB) of the catalyst sample of this Example 4 displayed an increase of 66%, and the Catalyst Activity was still 17.4% of that of Example 3.

Example 5

The catalyst sample of Example 1 was treated in nitrogen that was saturated with water vapor in accordance with Proton Content Adjustment Technique #2 at a Contact Temperature of 220° C. and a Contact Pressure of 50 psig. The resulting catalyst was then treated in accordance with Proton Content Adjustment Technique #1, to produce the treated catalyst sample of this Example 5 having a third hydration state. The proton density of the treated catalyst was 1.76 mmol per gram of catalyst (third hydration state), determined in accordance with the NMR Procedure for Determining Proton Density, described above, at the Specified NMR Pretreatment Temperature of 250° C.

A 0.5 gram portion of the treated catalyst of this Example 5 was tested in accordance with Catalyst Reactivity Testing Procedure at the Specified Ex-situ Drying Temperature of 250° C. and the Specified In-situ Drying Temperature of 170° C. The Catalyst Selectivity of the catalyst sample was 6.80, determined as the weight ratio of IPB/DIPB. The Catalyst Activity of this catalyst sample was 377.

The PDI of the catalyst sample of this Example 5 was determined to be 1.03, and represents a 3% increase in proton content (determined as mmol of protons per gram of catalyst), as compared to the catalyst sample of Example 1. The Catalyst Selectivity (IPB/DIPB) of the catalyst sample of this Example 5 displayed an increase of 15%, and the Catalyst Activity displayed an increase of 4%, as compared to the catalyst sample of Example 1.

Example 6

The catalyst sample of this Example 6 comprised 80 wt % MCM-49 and 20 wt % alumina and its proton density was determined in accordance with the NMR Procedure for Determining Proton Density, described above, at the Specified NMR Pretreatment Temperature of 150° C. The proton density was found to be 2.59 mmol per gram of catalyst (first hydration state).

A 0.5 gram portion of the catalyst sample of this Example 6 was tested in accordance with Catalyst Reactivity Testing Procedure at the Specified Ex-situ Drying Temperature of 150° C. and the Specified In-situ Drying Temperature of 150° C. The Catalyst Selectivity of this catalyst sample was 5.92, determined as the weight ratio of isopropylbenzene to diisopropylbenzene (IPB/DIPB). The Catalyst Activity of this catalyst sample was 275.

Example 7

Another portion of the catalyst sample of Example 6 was treated in accordance with Proton Content Adjustment Technique #1 at a Contact Time of approximately 1 hour, to produce the treated catalyst sample of this Example 7 having a third hydration state. The proton density of the treated catalyst was 3.16 mmol per gram of catalyst, determined in accordance with the NMR Procedure for Determining Proton Density, described above, at the Specified NMR Pretreatment Temperature of 150° C.

A 0.5 gram portion of the treated catalyst of this Example 7 was tested in accordance with Catalyst Reactivity Testing Procedure at the Specified Ex-situ Drying Temperature of 150° C. and the Specified In-situ Drying Temperature of 150° C. The Catalyst Selectivity of this catalyst sample was 7.81, determined as the weight ratio of IPB/DIPB. The Catalyst Activity of this catalyst was 251.

The PDI of the catalyst sample of this Example 7 was determined to be 1.22, and represents a 22% increase in proton content (determined as mol of protons per gram of catalyst), as compared to the catalyst sample of Example 6. The Catalyst Selectivity (IPB/DIPB) of the catalyst sample of Example 7 displayed an increase of 32%, and the Catalyst Activity decreased only slightly to 91% of that of the catalyst in Example 6.

Example 8

The catalyst sample of this example comprised 65 wt % MCM-22 and 35 wt % alumina and its proton density was determined in accordance with the NMR Procedure for Determining Proton Density, described above, at the Specified NMR Pretreatment Temperature of 250° C. The proton density was 1.46 mmol per gram of catalyst (first hydration state).

A 1.0 gram portion of the catalyst sample of this Example 8 was tested in accordance with Catalyst Reactivity Testing Procedure at the Specified Ex-situ Drying Temperature of 250° C. and the Specified In-situ Drying Temperature of 170° C. The Catalyst Selectivity of the catalyst sample was 5.46, determined as the weight ratio of isopropylbenzene to diisopropylbenzene (IPB/DIPB). The Catalyst Activity of this catalyst sample was 272.

Example 9

A portion of the catalyst sample of Example 8 that had become at least partially deactivated, such as if used commercially, was regenerated according to the following two-step procedure. First, the catalyst sample was heated to a temperature of 385° C. in an atmosphere having less than 2.0 vol. % hydrogen and hydrocarbons. The oxygen concentration was initially increased to 0.4 vol. %, and then increased again to 0.7 vol. % while the maximum catalyst temperature was maintained at 467° C. Second, the catalyst was heated to 450° C. in an atmosphere having an oxygen concentration of 0.7 vol. %, which was increased to 7.0 vol. % while the maximum catalyst temperature was maintained at 510° C.

This catalyst sample was then treated according to Proton Content Adjustment Technique #1 at a Contact Time of approximately 1 hour, to produce the treated catalyst of this Example 9 having a third hydration state. The proton density of the treated catalyst was 1.97 mmol per gram of catalyst (third hydration state), determined in accordance with the NMR Procedure for Determining Proton Density, described above, at the Specified NMR Pretreatment Temperature of 250° C.

A 1.0 gram portion of the treated catalyst sample of this Example 9 was tested in accordance with Catalyst Reactivity Testing Procedure at the Specified Ex-situ Drying Temperature of 250° C. and the Specified In-situ Drying Temperature of 170° C. The Catalyst Selectivity of this catalyst sample was 6.29, determined as the weight ratio IPB/DIPB. The Catalyst Activity of this catalyst sample was 174.

The PDI of the catalyst sample of Example 9 was determined to be 1.35, and represents a 35% increase in the proton content (determined as mmol of protons per gram of catalyst), as compared to the catalyst sample of Example 8. The Catalyst Selectivity (IPB/DIPB) of the catalyst sample of this Example 9 displayed a 15% increase, and the Catalyst Activity was still 64% of that of the catalyst of Example 8.

Example 10

The catalyst sample described in Example 6 was treated in accordance with Proton Content Adjustment Technique #2 at a Contact Temperature of 220° C. and a Contact Pressure of 50 psig in nitrogen that was saturated with water vapor. The resulting catalyst sample was then treated in accordance with to Proton Content Adjustment Technique #1, to produce the treated catalyst of this Example 10 having a third hydration state. The proton density of this treated catalyst sample was determined in accordance with the NMR Procedure for Determining Proton Density, described above, at the Specified NMR Pretreatment Temperature of 150° C. The proton density was 2.19 mmol per gram of catalyst (third hydration state).

A 0.5 gram portion of the treated catalyst sample of this Example 10 was tested in accordance with Catalyst Reactivity Testing Procedure at the Specified Ex-situ Drying Temperature of 150° C. and the Specified In-situ Drying Temperature of 150° C. The Catalyst Selectivity of this catalyst sample was 7.09, determined as the weight ratio IPB/DIPB. The Catalyst Activity of this catalyst sample was 244.

The PDI of the catalyst sample of this Example 10 was determined to be 1.03, and represents a 3% increase in the proton content (determined as mmol of protons per gram of catalyst) as compared to the catalyst sample of Example 6. The Catalyst Selectivity (IPB/DIPB) of the catalyst sample of Example 10 displayed an increase of 20%, and the catalyst activity decreased only slightly to 89% of that of the catalyst of Example 6.

Example 11 (Comparative)

The catalyst sample of this Example 11 comprised porous non-crystalline tungsten-zirconia ($WZrO_2$) and its proton density was determined in accordance with the NMR Procedure for Determining Proton Density, described above, at the Specified NMR Pretreatment Temperature of 250° C. The proton density was 0.37 mmol per gram of catalyst (first hydration state).

A 0.5 gram portion of the catalyst sample of this Example 11 was tested in accordance with Catalyst Reactivity Testing Procedure at the Specified Ex-situ Drying Temperature of 250° C. and the Specified In-situ Drying Temperature of 170° C. The Catalyst Selectivity was 13.70, determined as the weight ratio of isopropylbenzene to diisopropylbenzene (IPB/DIPB). The Catalyst Activity of this catalyst sample was 1.

Example 12 (Comparative)

The catalyst sample of Example 11 was treated in accordance with the Proton Content Adjustment Technique #1 at a Contact Time of approximately 1 hour, to produce a treated catalyst sample of this Example 12 having a third hydration state. The proton density of the treated catalyst sample was 0.41 mmol per gram of catalyst (third hydration state), determined in accordance with the NMR Procedure for Determining Proton Density, described above, at the Specified NMR Pretreatment Temperature of 250° C.

A 0.5 gram portion of the treated catalyst of this Example 12 was tested in accordance with Catalyst Reactivity Testing Procedure at the Specified Ex-situ Drying Temperature of 250° C. and the Specified In-situ Drying Temperature of 170° C. The Catalyst Selectivity of this catalyst sample was 9.62, determined as the weight ratio IPB/DIPB. The Catalyst Activity of this catalyst sample was 1.

The PDI of the catalyst sample of Example 12 was determined to be 1.11, and represents an 11% increase in the proton content (determined as mmol of protons per gram of catalyst), as compared to the catalyst of Example 11. However, the Catalyst Selectivity (IPB/DIPB) of the catalyst sample of this Example 12 displayed a 29.8% decrease, as compared to the catalyst sample of Example 11. The Catalyst Activity was 100% of the catalyst sample of Example 11.

Non-limiting examples of the invention involving an oligomerization reaction mechanism are presented herein as follows:

Example 13

A 0.5 gram portion of the catalyst sample of Example 1 (first hydration state) was placed in the batch reactor as described in the Catalyst Reactivity Testing Procedure, described above, with the exception that no benzene was used and the propylene content was increased. The Specified Ex-situ Drying Temperature was 250° C. and the Specified In-situ Drying Temperature was 170° C. The catalyst sample was contacted with 56.2 grams propylene at a temperature of 25° C. and pressure of 300 psig. After a 4 hour reaction time, the oligomerization product was collected and shown by GC analysis to have an average molecular weight of 161.3, with the product comprising 1.01 wt. % C6, 34.24 wt. % C9, 32.45 wt. % C12 oligomers, plus other reaction by-products.

Example 14

A 0.5 gram portion of the treated catalyst sample of Example 2 (third hydration state) was placed in the batch reactor as described in the Catalyst Reactivity Testing Procedure, described above, with the exception that no benzene was used and the propylene content was increased. The Specified Ex-situ Drying Temperature was 250° C. and the Specified In-situ Drying Temperature was 170° C. The catalyst sample was contacted with 56.2 grams propylene at a temperature of 25° C. and pressure of 300 psig. After a 4 hour reaction time, the oligomerization product was collected and shown by GC analysis to have an average molecular weight of 152.2, with the product comprising 11.02 wt. % C6, 34.99 wt. % C9, 26.74 wt. % C12 oligomers, plus other reaction by-products.

All patents, patent applications, test procedures, priority documents, articles, publications, manuals, and other documents cited herein are fully incorporated by reference for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A process for catalytic conversion of feedstock comprising at least one alkylatable aromatic compound and an alkylating agent to conversion product which comprises an alkylaromatic compound, said process comprising the step of contacting said feedstock under catalytic conversion conditions including a temperature of from about 0° C. to about 1000° C., a pressure of from about 0.1 atmosphere to about 1000 atmospheres, and a feed weight hourly space velocity (WHSV) of from about 0.01 to 500 $hr^{-1}$ or a reaction time of from about 1 minute to about 100 hours with a catalyst composition comprising an acidic, porous crystalline material, wherein said catalyst composition is produced by the steps of:
   (a) providing a first catalyst comprising said acidic, porous crystalline material, said first catalyst having a first proton density;
   (b) contacting said first catalyst of step (a) with water in liquid form at a contact temperature from about 1° C. to about 99° C., to add protons and generate a second catalyst having a second proton density, wherein the value of said second proton density is greater than said value of said first proton density when said values are measured under the same conditions; and
   (c) drying said second catalyst of step (b) at a drying temperature of up to about 550° C., to remove at least a portion of said protons from said second catalyst and generate said catalyst composition having a third proton density, wherein the value of said third proton density is between said value of said first proton density and said value of said second proton density when said values are measured under the same conditions,
   wherein said acidic, porous crystalline material is selected from the group consisting of MCM-22, MCM-49, zeolite beta and mixtures thereof.

2. The process of claim 1, wherein said conversion conditions include a temperature of from about 0° C. to about 500° C., a pressure of from about 0.2 to about 250 atmospheres, a molar ratio of alkylatable aromatic compound to alkylating agent of from about 0.1:1 to about 50:1, and a feed weight hourly space velocity (WHSV) based on the alkylating agent of from about 0.1 to about 500 $hr^{-1}$.

3. The process of claim 1, wherein said alkylatable aromatic compound is selected from the group consisting of benzene, naphthalene, anthracene, naphthacene, perylene, coronene, phenanthrene and mixtures thereof.

4. The process of claim 1, wherein said alkylatable aromatic compound is benzene and said alkylating agent is selected from the group consisting of ethylene, propylene and the butenes.

5. The process of claim 1, wherein said alkylatable aromatic compound is benzene and said alkylating agent is ethylene, said alkylated aromatic compound comprises ethylbenzene, and said conversion conditions include a temperature of from about 150° C. to about 300° C.; a pressure up to about 200 atmospheres; a weight hourly space velocity (WHSV) based on the ethylene alkylating agent of from about 0.1 to about 20 $hr^{-1}$; and a ratio of benzene to ethylene in the alkylation reactor of from about 0.5:1 to about 30:1 molar.

6. The process of claim 1, wherein said alkylatable aromatic compound is benzene and said alkylating agent is propylene, said alkylated aromatic compound comprises cumene, and said conversion conditions include a temperature of up to about 250° C., a pressure of about 250 atmospheres or less, a weight hourly space velocity (WHSV) based on propylene alkylating agent of from about 0.1 $hr^{-1}$ to about 250 $hr^{-1}$, and a ratio of benzene to propylene in the alkylation reactor of from about 0.5:1 to about 30:1 molar.

7. The process of claim 1, wherein said alkylatable aromatic compound is benzene and said alkylating agent is selected from the group consisting of 1-butene, 2-butene and mixtures thereof, said alkylated aromatic compound comprises sec-butylbenzene, said conversion conditions include a temperature of about 50 to about 250° C., a pressure of about 3.5 to about 35 atmospheres, a weight hourly space velocity (WHSV) based on alkylating agent of from about 0.1 $hr^{-1}$ to about 20 $hr^{-1}$, and a ratio of benzene to said alkylating agent in the alkylation reactor of from about 1:1 to about 10:1 molar.

8. The process of claim 5, wherein the conversion product further comprises polyalkylated aromatic compounds, said process further comprising contacting the polyalkylated aromatic compounds with benzene under transalkylation conditions and in the presence of a transalkylation catalyst, to produce additional ethylbenzene, said transalkylation catalyst selected from the group consisting of zeolite Beta, zeolite Y, mordenite, TEA-mordenite, MCM-22, PSH-3, SSZ-25, ERB-1, ITQ-1, ITQ-2, ITQ-30, MCM-36, MCM-49, MCM-56 and mixtures thereof.

9. The process of claim 6, wherein the conversion product further comprises polyalkylated aromatic compounds, said process further comprising contacting the polyalkylated aromatic compounds with benzene under transalkylation conditions and in the presence of a transalkylation catalyst, to produce additional cumene, said transalkylation catalyst selected from the group consisting of zeolite Beta, zeolite Y, mordenite, TEA-mordenite, MCM-22, PSH-3, SSZ-25, ERB-1, ITQ-1, ITQ-2, ITQ-30, MCM-36, MCM-49, MCM-56 and mixtures thereof.

10. The process of claim 7, wherein the conversion product further comprises polyalkylated aromatic compounds, said process further comprising contacting the polyalkylated aromatic compounds with benzene under transalkylation conditions and in the presence of a transalkylation catalyst, to produce additional sec-butylbenzene, said transalkylation catalyst selected from the group consisting of zeolite Beta, zeolite Y, mordenite, TEA-mordenite, MCM-22, PSH-3, SSZ-25, ERB-1, ITQ-1, ITQ-2, ITQ-30, MCM-36, MCM-49, MCM-56 and mixtures thereof.

11. The process of claim 5, wherein the conversion product further comprises polyalkylated aromatic compounds, said process further comprising contacting the polyalkylated aromatic compounds with benzene under transalkylation conditions and in the presence of a treated transalkylation catalyst, to produce additional ethylbenzene, and
wherein said treated transalkylation catalyst is produced by the steps of:
  (i) providing an first transalkylation catalyst which comprises an acidic, porous crystalline material selected from the group consisting of zeolite Beta, zeolite Y, mordenite, TEA-mordenite, MCM-22, PSH-3, SSZ-25, ERB-1, ITQ-1, ITQ-2, ITQ-30, MCM-36, MCM-49, MCM-56 and mixtures thereof, said first transalkylation catalyst having a first proton density;
  (ii) contacting said first transalkylation catalyst of step (i) with water in liquid or gaseous form at a contact temperature up to about 500° C., to add protons and generate a second transalkylation catalyst having a second proton density, wherein the value of said second proton density is greater than said value of said first proton density when said values are measured under the same conditions; and
  (iii) drying said second transalkylation catalyst of step (ii) at a drying temperature of up to about 550° C., to remove at least a portion of said protons from said second transalkylation catalyst and generate said treated transalkylation catalyst having a third proton density, wherein the values of said third proton density is between said value of said first proton density and said value of said second proton density when said values are measured under the same conditions.

12. The process of claim 6, wherein the conversion product further comprises polyalkylated aromatic compounds, said process further comprising contacting the polyalkylated aromatic compounds with benzene under transalkylation conditions and in the presence of a treated transalkylation catalyst, to produce additional cumene, and
wherein said treated transalkylation catalyst is produced by the steps of:
  (i) providing an first transalkylation catalyst which comprises an acidic, porous crystalline material selected from the group consisting of zeolite Beta, zeolite Y, mordenite, TEA-mordenite, MCM-22, PSH-3, SSZ-25, ERB-1, ITQ-1, ITQ-2, ITQ-30, MCM-36, MCM-49, MCM-56 and mixtures thereof, said first transalkylation catalyst having a first proton density;
  (ii) contacting said first transalkylation catalyst of step (i) with water in liquid or gaseous form at a contact temperature up to about 500° C., to add protons and generate a second transalkylation catalyst having a second proton density, wherein the value of said second proton density is greater than said value of said first proton density when said values are measured under the same conditions; and
  (iii) drying said second transalkylation catalyst of step (ii) at a drying temperature of up to about 550° C., to remove at least a portion of said protons from said second transalkylation catalyst and generate said treated transalkylation catalyst having a third proton density, wherein the values of said third proton density is between said value of said first proton density and said value of said second proton density when said values are measured under the same conditions.

13. The process of claim 7, wherein the conversion product further comprises polyalkylated aromatic compounds, said process further comprising contacting the polyalkylated aromatic compounds with benzene under transalkylation conditions and in the presence of a treated transalkylation catalyst, to produce additional sec-butylbenzene, and wherein said treated transalkylation catalyst is produced by the steps of:
(i) providing an first transalkylation catalyst which comprises an acidic, porous crystalline material selected from the group consisting of zeolite Beta, zeolite Y, mordenite, TEA-mordenite, MCM-22, PSH-3, SSZ-25, ERB-1, ITQ-1, ITQ-2, ITQ-30, MCM-36, MCM-49, MCM-56 and mixtures thereof, said first transalkylation catalyst having a first proton density;
(ii) contacting said first transalkylation catalyst of step (i) with water in liquid or gaseous form at a contact temperature up to about 500° C., to add protons and generate a second transalkylation catalyst having a second proton density, wherein the value of said second proton density is greater than said value of said first proton density when said values are measured under the same conditions; and
(iii) drying said second transalkylation catalyst of step (ii) at a drying temperature of up to about 550° C., to remove at least a portion of said protons from said second transalkylation catalyst and generate said treated transalkylation catalyst having a third proton density, wherein the values of said third proton density is between said value of said first proton density and said value of said second proton density when said values are measured under the same conditions.

* * * * *